United States Patent [19]

Orenga

[11] Patent Number: 6,046,016
[45] Date of Patent: Apr. 4, 2000

[54] METHOD FOR DEMONSTRATING AN ENZYMATIC ACTIVITY OF MICRO-ORGANISMS

[75] Inventor: Sylvain Orenga, Neuville S/Ain, France

[73] Assignee: Bio Merieux, Marcy L'Etoile, France

[21] Appl. No.: 09/043,191

[22] PCT Filed: Jul. 29, 1997

[86] PCT No.: PCT/FR97/01415

§ 371 Date: Apr. 27, 1998

§ 102(e) Date: Apr. 27, 1998

[87] PCT Pub. No.: WO98/04735

PCT Pub. Date: Feb. 5, 1998

[30] Foreign Application Priority Data

Jul. 29, 1996 [FR] France .................................. 96 09523

[51] Int. Cl.⁷ .............................. C12Q 1/02; C12Q 1/37; C12N 5/00
[52] U.S. Cl. ................................. 435/24; 435/4; 435/19; 435/29; 435/34; 436/63; 436/164; 436/166; 436/172
[58] Field of Search .................................. 435/4, 19, 24, 435/29, 34, 243; 436/62, 164, 166, 172

[56] References Cited

U.S. PATENT DOCUMENTS

| | | | |
|---|---|---|---|
| 4,278,763 | 7/1981 | Berger et al. .............................. | 435/23 |
| 5,336,600 | 8/1994 | Monget ...................................... | 435/34 |
| 5,434,056 | 7/1995 | Monget et al. ............................ | 435/14 |

FOREIGN PATENT DOCUMENTS

| | | |
|---|---|---|
| WO 90-12888 | 11/1990 | WIPO . |
| WO 92-12259 | 7/1992 | WIPO . |

OTHER PUBLICATIONS

Logda, Z. et al. "The Histochemical Demonstration of Aminopeptidase with Bromoindolyl Leucinamide." *Histochemistry*, vo. 43, 1975, pp. 355–366.
Rath, J. et al. "Ectoenzymatic Activity and Bacterial Dynamics along a Tropic Gradient in the Caribbean Sea." *Marine Ecology Progress Series*, vol. 102, 1993, pp. 89–96.
Yarborough et al., Histochemistry of Macrophage Hydrolases, III. Studies on β–Galactosidase, β–Glucuronidase and Aminopeptidase with Indolyl and Naphthyl Substrates, Journal of the Reticuloendothelial Society 4, pp. 390–408 (1967).
Lojda et al., The Histochemical Demonstration of Aminopeptidase With Bromoindolyl Leueinamide, Histochemistry 43, pp. 355–366 (1975).
Pearson et al., The Histochemical Demonstration of Leucine Aminopeptidase by Means of a New Indolyl Compound, Histochemistry of Leucine Aminopeptidase vol. 12, No. 7 pp. 712–720 (1963).

*Primary Examiner*—Leon B. Lankford, Jr.
*Assistant Examiner*—Christopher R. Tate
*Attorney, Agent, or Firm*—Oliff & Berridge, PLC

[57] ABSTRACT

The method consists in the use of one compound of formula: X—NH—R in which X represents one 5-bromoindole-3-yle group and R represents the acyl radical of one amino acid selected between leucine and alanine, as tracer for demonstrating, by the formation of a colored product, a peptidase activity in a culture of micro-organisms.

8 Claims, No Drawings

METHOD FOR DEMONSTRATING AN ENZYMATIC ACTIVITY OF MICRO-ORGANISMS

The present invention relates to a method for demonstrating an enzymatic activity of microorganisms. Such a method can be used for the identification of microorganisms which may or may not express this enzymatic activity.

The detection and identification of micro-organisms are very important especially in medicine, in the agrifoods industry, for environmental control (for example for controlling water, etc.). Micro-organisms may be desired for their pathogenicity, as contamination indicators, or alternatively for controlling manufacturing processes.

The techniques for detecting and identifying microorganisms are currently based on the search for characteristic nucleotide sequences, the search for antigens or antibodies, culturing in a selective or non-selective medium, or alternatively the search for metabolic and especially enzymatic activities (for example osidase, esterase, peptidase, oxidase etc. activities).

Usually, the methods for detecting and identifying microorganisms combine several of these techniques. Thus, culturing is used to multiply and select the desired microorganisms. In order to simplify their detection, it has been proposed to demonstrate biochemical activities by introducing molecules which produce a coloration or a fluorescence, directly into the culture medium. Such media are referred to as detection media. The biochemical activities can be demonstrated by various methods such as:

physicochemical modification of the medium: change of pH revealed using a coloured or fluorescent indicator (methylumbelliferone), change of the redox potential revealed using a coloured indicator (tetrazolium salt) or a fluorescent indicator, reaction of a molecule produced by the microorganisms with a compound present in the medium, leading to a coloration, hydrolysis of molecules releasing a coloured or fluorescent compound (naphthol, coumarin).

The hydrolyses detected are generally the result of the action of an enzyme produced by the microorganism on a natural or synthetic enzymatic substrate. These enzymatic activities are, for example, those of the following enzymes: esterases (for example lipases, phosphatases), osidases (β-galactosidase, β-glucuronidase, N-acetyl-hexosaminidase), peptidases (alanine-aminopeptidase, trypsinase, gelatinase), DNAses, decarboxylases, deaminases, ureases, tryptophanases, oxidases, catalases, etc.

It is known that gelled media are particularly suitable for culturing and isolating microorganisms from a sample, as well as for detecting "target" microorganisms in a mixture of microorganisms. On these media, the microorganisms form colonies that can be detected with the naked eye, and it is highly desirable for the products of the biochemical activities studied to remain localized at their site of production. This effectively makes it possible to distinguish one colony from its neighbours if they do not express the same activities. Various detection methods can thus be used, for example changes in pH (FR-A-2,671,100), esterase activities (FR-2-457,323), osidase activities (FR-A-2,684,110), etc. Needless to say, it is possible to use several of these methods in conjunction, in order to demonstrate several species or strains, and/or in order to increase the sensitivity and/or specificity of the detection.

There are currently no means available, which are suitable for gelled media, for demonstrating the activities of L-alanine-aminopeptidases, D-alanine-aminopeptidases and L-leucine-aminopeptidases of microorganisms. The reason for this is that the enzyme substrates used to date release coloured or fluorescent molecules which diffuse into the gelled media and/or which are only revealed by UV irradiation (in the case of naphthylamine or aminocoumarin) and/or after the action of reagents (in the case of naphthylamine), or whose coloration is of relatively poor contrast in the reaction media used in microbiology (in the case of nitroaniline).

It is known that L-leucine-aminopeptidase has been demonstrated in mammalian histological sections by means of an enzyme substrate, L-leucine-3-(5-bromoindolamine), known as L-Leu-BIA for short, which produces a coloured compound after hydrolysis; see Pearson et al., 1963, Lab. Invest., 12: 712, who called this compound L-N-(5-bromoindol-3-yl) (leucinamide hydrobromide). In 1967, Yarborough et al., J. Reticuloendoth. Soc., 4: 390 repeated the technique of Pearson et al. in similar applications (histological slices). They pointed out that adding a mixture of potassium ferr- or ferrocyanide or copper sulphate inhibits the reaction.

In 1975, Lojda and Havränkovä, Histochemistry, 43: 355 proposed to improve the method using the substrate L-Leu-BIA by adding a mixture of tetrazolium salt and phenazine methosulphate, the coloured reaction observed being derived, in this case, from reduction of the tetrazolium salt to formazan.

In the course of the studies which lead to the present invention, an investigation was carried out as to whether it was possible to use L-Leu-BIA as an enzyme substrate in the detection of microorganisms cultured in particular on gelled media. During preliminary tests, L-Leu-BIA was added to the medium described in Example 1 below. This medium is commonly used to search for osidases.

It was not possible to demonstrate a peptidase activity, irrespective of the microorganism cultured in this medium (*Escherichia coli*, Klebsiella, Citrobacter, Pseudomonas, Enterococcus, Staphylococcus, Streptococcus) .

On the other hand, if L-leucine-7-amino-4-methylcoumarin (L-Leu-AMC) is added to this same medium, a fluorescence is detected with some of these microorganisms. Similarly, in this medium, with osidase substrates (5-bromo-4-chloro-3-indolyl-β-D-galactoside and 6-chloro-3-indolyl-β-D-glucuronide), the β-galactosidase and β-glucuronidase activities of the microorganisms can be detected. Addition of the reagents proposed by Lojda and Havränkovä was reflected by a more or less complete inhibition of the growth of the microorganisms without allowing the revelation of a peptidase activity with L-Leu-BIA.

Similarly, with the medium used in Example 2 below, it was not possible to demonstrate a peptidase activity with L-Leu-BIA, whereas the substrate L-Leu-AMC allows this activity to be detected in the same medium.

It has now been discovered that the absence of results with the BIA derivatives was not due to an incompatibility with the microorganisms or to an inhibition of their multiplication during culturing, but was due essentially to the conditions of the medium. Indeed, it has been discovered that it was possible to reveal the peptidase activity of microorganisms with L-Leu-BIA by using other culture media. The reasons for which certain media can be used and others cannot are unknown. Nevertheless, it is possible to determine and develop, by simple routine experiments similar to those described in the experimental section below, media and/or ingredients which are suitable or which are unsuitable. The invention thus consisted firstly, in particular, in searching for, and in showing that it was possible to find, culture media in which the 5-bromoindolamine-derived peptidase substrates mentioned above can be used to demonstrate the corresponding enzymatic activities in a microorganism culture.

It has thus been discovered in particular that the following medium can be used:

| | |
|---|---|
| Yeast extract | 0.5–25 g/l |
| Gelatin peptone | 0.5–25 g/l |
| NaCl | 0–50 g/l |
| and optionally: | |
| pH regulator, q.s. pH = 3 to 9 | |
| and/or: | |
| Gelling agent | 5–35 g/l |

The pH chosen is a pH which is suitable for the microorganism studied. In the case of a gelled medium, the pH is preferably from 5 to 9. The pH can be adjusted, for example, using hydrochloric acid or sodium carbonate.

If L-Leu-BIA is added to such a medium, and inoculation with microorganisms is carried out, after culturing, brown or colourless colonies are obtained depending on whether the microorganisms do or do not express an L-leucine-aminopeptidase activity.

Comparable results have been obtained with the substrates L-Ala-BIA and D-Ala-BIA.

The subject of the invention is thus the use of at least one compound of formula:

X—NH—R in which X represents a 5-bromoindole-3-yl group and R represents the acyl residue of an amino acid chosen from leucine and alanine, as a tracer which makes it possible to demonstrate, by formation of a coloured product, a peptidase activity in a microorganism culture.

In particular, the group R represents an acyl residue of L-Leu, L-Ala or D-Ala.

The substrates whose use forms the subject of the present application do not inhibit the multiplication of microorganisms in the appropriate culture media. The tracer can thus be used by adding it to the microorganism culture medium, before the start of culturing or at the start of culturing.

One of the important advantages of the tracers used according to the invention is that in the presence of the peptidase activity investigated, they give coloured products which do not diffuse into the gelled medium.

They can thus be used in a gelled medium. They can, of course, also be used in a liquid medium.

According to a specific embodiment, at least one other tracer which makes it possible to demonstrate, by formation of a coloured or fluorescent product, an enzymatic activity which is generally different from that demonstrated using the compounds of formula X—NH—R as defined above can also be added to the culture. This can be, for example, an esterase, osidase or peptidase activity. Additional information can thus be obtained, in association with an absence of coloration (or of fluorescence) or in association with a coloration which is modified relative to the coloration obtained with only one enzyme substrate. The tracer chosen will have different properties from those of the BIA derivatives: for example, another tracer capable of giving a reaction product having a different colour from the brown colour obtained with the BIA derivatives will be chosen. The other tracer (or second tracer) will thus make it possible to reveal, by virtue of its intrinsic colour, or by virtue of its fluorescence, the presence of an enzymatic activity for which it is specific. If the peptidase activity which can be revealed by the BIA derivatives is also present, a modified coloration, different from the said brown colour and also different from the said intrinsic colour given by the second tracer, will be obtained. Examples of the use of several substrates, as well as the information which can be derived therefrom, are given below in the experimental section. Needless to say, the results can vary with each species or strain of microorganism studied.

Each case liable to be of interest must thus undergo prior studies according to routine experiments.

The derivatives used to demonstrate various enzymatic activities, and which can be used as other tracers, are, in particular, indoxyl, coumarin, resorufin, naphthol, naphthylamine, nitrophenol, nitroaniline, rhodamine, hydroxyquinoline, fluorescein etc. derivatives Among these derivatives which can be used in combination with the BIA derivatives, mention may be made in particular of 5-bromo-4-chloro-3-indolyl-β-D-glucuronide, 6-chloro-3-indolyl-β-D-glucoside, L-alanine-7-amino-4-methylcoumarin, 4-methylumbelliferyl-N-acetyl-β-D-galactosaminide, resorufin-β-D-galactoside, β-naphthyl sulphate, AS-BI β-D-galactoside naphthol, L-alanineβ-naphthylamide, o-nitrophenol-β-D-galactoside, carboxybenzoyl-L-arginine-p-nitroanilide, rhodamine-110-bis(L-leucine amide), hydroxyquinoline-β-D-glucoside and fluorescein diacetate.

The subject of the invention is also a process for demonstrating a peptidase activity in a microorganism culture, in which a tracer which makes it possible to demonstrate the said activity, by formation of a coloured product, is added to the culture medium of the said microorganisms, characterized in that the said tracer comprises at least one compound of formula:

X—NH—R, in which X and R are defined as above.

The compound X—NH—R can be added before the start of culturing or during culturing, or even at the end of culturing. The use of the method of the invention thus involves culturing the microorganisms studied, it being understood that this culturing can be carried out before or after addition of the compound X—NH—R, and that this addition can also be carried out during culturing. Needless to say, the actual culturing is carried out by incubation of a suitable culture medium under conditions which allow the microorganisms studied to multiply. The compositions of the culture media and the culturing conditions which are suitable are known or can be determined by routine experiments.

The subject of the invention is also a culture medium for microorganisms containing, besides the necessary ingredients for culturing the said microorganisms, at least one compound of formula X—NH—R.

The derivatives of formula X—NH—R are used at concentrations that are sufficient to give observable coloured reactions. These concentrations, which can be determined by routine experiments, can generally vary from 25 to 2000 mg per litre of culture medium.

The characteristics and advantages of the invention are illustrated by the following examples.

EXAMPLES

Example 1

The culture medium contains, besides water:

| | |
|---|---|
| Meat peptone* | 15 g/l |
| Casein peptone** | 3 g/l |
| NaCl | 5 g/l |
| Tris buffer | 0.5 g/l |

-continued

| | |
|---|---|
| Na$_2$HPO$_4$ | 1 g/l |
| Sodium citrate | 1 g/l |
| Glucose | 1 g/l |
| Sodium pyruvate | 2 g/l |
| Agar | 13 g/l |

*Sold by D.I.F.C.O.
**Sold by D.I.F.C.O.

L-Ala-BIA, L-Leu-BIA, L-Ala-AMC or L-Leu-AMC is added to this medium at concentrations of 200 mg/l. The various media obtained, distributed in Petri dishes, are inoculated with microorganisms. The dishes were incubated at 37° C. for 48 hours. The colonies formed were examined visually in ambient light and under a UV lamp (wavelength= 365 nm) after incubation for 24 and 48 hours. The colour or the presence of fluorescence were noted. The microorganisms studied were: *Escherichia coli, Klebsiella pneumoniae, Citrobacter freundii, Pseudomonas aeruginosa, Streptococcus agalactiae, Enterococcus faecium, Streptococcus pyogenes, Staphylococcus epidermidis* and *Candida albicans*. The results are presented in Table I below:

TABLE I

| Strains | | L-Ala—AMC | L-Ala—BIA | L-Leu—AMC | L-Leu—BIA |
|---|---|---|---|---|---|
| *E. coli* | 24 h | Fluo[1] | —[2] | Fluo | — |
| | 48 h | Fluo | — | Fluo | — |
| *K. pneumoniae* | 24 h | Fluo | — | Fluo | — |
| | 48 h | Fluo | — | Fluo | — |
| *C. freundii* | 24 h | Fluo | — | Fluo | — |
| | 48 h | Fluo | — | Fluo | — |
| *P. aeruginosa* | 24 h | Fluo | — | — | — |
| | 48 h | Fluo | — | Fluo | — |
| *S. agalactiae* | 24 h | — | — | Fluo | — |
| | 48 h | Fluo | — | Fluo | — |
| *E. faecium* | 24 h | — | — | — | — |
| | 48 h | Fluo | — | Fluo | — |
| *S. pyogenes* | 24 h | — | — | Fluo | — |
| | 48 h | Fluo | — | Fluo | — |
| *S. epidermidis* | 24 h | — | — | — | — |
| | 48 h | — | — | — | — |
| *C. albicans* | 24 h | — | — | NT[3] | NT |
| | 48 h | Fluo | — | NT | NT |

[1]Fluo = fluorescence
[2]— = absence of fluorescence and/or absence of coloration
[3]NT = not tested The medium used in this example makes it possible to demonstrate the L-alanine-aminopeptidase and L-leucine-aminopeptidase activities with the reagents L-Ala-AMC and L-Leu-AMC respectively, but when L-Ala-BIA and L-Leu-BIA are used, no hydrolysis is detected.

Example 2

L-Leu-BIA or L-Leu-AMC is added to a 0.1 M, pH 7.3 phosphate buffer at 25° C., to concentrations of 400 mg/l. The media obtained were distributed into microtitration plate wells and inoculated with microorganism suspensions. The plates were incubated for 24 hours at 37° C. The wells were examined visually in ambient light and under a UV lamp, as above. After incubation for 24 and 48 hours, the colour of the presence of fluorescence were noted. The results are presented in Table II below:

TABLE II

| Strain | | L-Leu—AMC | L-Leu—BIA |
|---|---|---|---|
| *E. coli* | 24 h | Fluo[1] | —[2] |
| | 48 h | Fluo | — |
| *K. pneumoniae* | 24 h | Fluo | — |
| | 48 h | Fluo | — |
| *C. freundii* | 24 h | Fluo | — |
| | 48 h | Fluo | — |
| *P. aeruginosa* | 24 h | — | — |
| | 48 h | Fluo | — |
| *S. agalactiae* | 24 h | Fluo | — |
| | 48 h | Fluo | — |
| *E. faecium* | 24 h | — | — |
| | 48 h | Fluo | — |
| *S. pyogenes* | 24 h | Fluo | — |
| | 48 h | Fluo | — |
| *S. epidermidis* | 24 h | — | — |
| | 48 h | — | — |

[1]Fluo = fluorescence
[2]— = absence of fluorescence and/or absence of coloration Thus, with the medium used in this example, it is possible to demonstrate the L-leucine-aminopeptidase activity with L-Leu-AMC, but when L-Leu-BIA is used, no hydrolysis is detected.

Example 3

The culture medium contains, besides water:

| | |
|---|---|
| Yeast extract* | 6 g/l |
| Gelatin peptone** | 5 g/l |
| NaCl | 8 g/l |
| Na$_2$CO$_3$ | 0.1 g/l |
| Agar | 13 g/l |

*Sold by Bio Mérieux
**Bio-gelytone sold by Bio Mérieux

L-Ala-BIA, L-Leu-BIA, L-Ala-AMC or L-Leu-AMC is added to this medium, to concentrations of 200 mg/l. The various media obtained, distributed in Petri dishes, are inoculated with the same microorganisms as those used in Example 1. The dishes are incubated at 370° C. for 48 hours. The colonies formed were examined visually in ambient light and under a UV lamp (wavelength=365 nm) after incubation for 24 and 48 hours. The colour or the presence of fluorescence were noted. The results are presented in Table III below:

TABLE III

| Strains | | L-Ala—AMC | L-Ala—BIA | L-Leu—AMC | L-Leu—BIA |
|---|---|---|---|---|---|
| E. coli | 24 h | Fluo[1] | Brown | Fluo | —[2] |
| Gram-negative | 48 h | Fluo | Brown | Fluo | Brown |
| K. pneumoniae | 24 h | Fluo | Brown | Fluo | — |
| Gram-negative | 48 h | Fluo | Brown | Fluo | Brown |
| C. freundii | 24 h | Fluo | Brown | Fluo | Brown |
| Gram-negative | 48 h | Fluo | Brown | Fluo | Brown |
| P. aeruginosa | 24 h | Fluo | Brown | — | — |
| Gram-negative | 48 h | Fluo | Brown | Fluo | Brown |
| S. agalactiae | 24 h | — | — | Fluo | — |
| Gram-positive | 48 h | Fluo | Brown | Fluo | — |
| E. faecium | 24 h | — | — | — | — |
| Gram-positive | 48 h | Fluo | Brown | Fluo | — |
| S. pyogenes | 24 h | — | — | Fluo | — |
| Gram-positive | 48 h | Fluo | Brown | Fluo | — |
| S. epidermidis | 24 h | — | — | — | — |
| Gram-positive | 48 h | — | — | — | — |
| C. albicans | 24 h | — | — | NT[3] | NT |
| | 48 h | Fluo | Brown | NT | NT |

[1]Fluo = fluorescence
[2]— = absence of fluorescence and/or absence of coloration
[3]NT = not tested The medium used in this example makes it possible to demonstrate the L-alanine-aminopeptidase and L-leucine-aminopeptidase activities with L-Ala-AMC and L-Leu-AMC respectively, as well as with L-Ala-BIA and L-Leu-BIA. However, these last two substrates give reactions that are occasionally delayed. On the other hand, they allow Gram-negative bacteria to be distinguished from Gram-positive bacteria. Indeed:

after incubation for 24 hours with L-Ala-BIA, the Gram-positive bacteria give no coloration, whereas the Gram-negative bacteria give a brown coloration; and after 48 hours with L-Leu-BIA, the Gram-positive bacteria give no coloration, whereas the Gram-negative bacteria give a brown coloration.

Example 4

L-Leu-BIA or L-Ala-BIA was added, alone or in combination with 5-bromo-4-chloro-3-indolyl-β-D-glucoside (X-Glu), 6-chloro-3-indolyl-β-D-glucoside (Z-Glu), 4-methylumbelliferyl-β-D-glucoside (MUGI) or 5-bromo-4-chloro-3-indolyl-acetate (X-Ac), to the medium of Example 3.

The concentrations of these various substrates are as follows:

L-Leu-BIA: 200 mg/l

L-Ala-BIA: 200 mg/l

X-Glu: 200 mg/l

Z-Glu: 200 mg/l

MuGI: 200 mg/l

These various media, distributed in Petri dishes, are inoculated with microorganisms. The strains studied are the same as those in the above examples. The dishes were incubated at 370° C. for 48 hours, and the colonies formed were examined visually in ambient light and under a UV lamp (wavelength=365 nm). The results of observation of the colour of the colonies obtained after incubation for 24 and 48 hours are presented in Table IV:

TABLE IV

| | | L-Ala—BIA | | | | | L-Leu—BIA | | | | |
|---|---|---|---|---|---|---|---|---|---|---|---|
| Strains | Medium No. | —<br>1 | X-Glu<br>2 | Z-Glu<br>3 | MUGI<br>4 | X-Ac<br>5 | —<br>6 | X-Glu<br>7 | Z-Glu<br>8 | MUGI<br>9 | X-Ac<br>10 |
| E. coli | 24 h | Brown | Brown | Brown | Brown | Brown | — | — | — | — | — |
| Gram-negative | 48 h | Brown | Brown | Brown | Brown | Brown | Brown | Brown | Brown | Brown | Brown-grey |
| K. pneumoniae | 24 h | Brown | Grey | Pink-grey | Brown + Fluo | Grey | — | Blue | Pink-grey | Fluo | Brown-grey |
| Gram-negative | 48 h | Brown | Grey | Pink-grey | Brown + Fluo | Grey brown | Brown | Blue-grey | Pink-Grey | Brown + Fluo | Brown-grey |
| C. freundii | 24 h | Brown | Grey | Pink-grey | Brown + Fluo | Grey | Brown | Grey | Pink-grey | Brown + Fluo | Brown-grey |
| Gram-negative | 48 h | Brown | Grey | Pink-grey | Brown + Fluo | Brown | Brown | Grey | Pink-grey | Brown + Fluo | Brown-grey |
| P. aeruginosa | 24 h | Brown | Brown | Brown | Brown | Brown-grey | — | — | — | — | — |
| Gram-negative | | | | | | | | | | | |

TABLE IV-continued

| Strains | Medium No. | L-Ala—BIA | | | | | L-Leu—BIA | | | | |
|---|---|---|---|---|---|---|---|---|---|---|---|
| | | — 1 | X-Glu 2 | Z-Glu 3 | MUGI 4 | X-Ac 5 | — 6 | X-Glu 7 | Z-Glu 8 | MUGI 9 | X-Ac 10 |
| | 48 h | Brown | Brown | Brown | Brown | Brown-grey | Brown | Brown | Brown | Brown | Brown-grey |
| S. agalactiae | 24 h | — | — | — | — | — | — | — | — | — | — |
| | 48 h | Brown | Brown | Brown | Brown | Grey | — | — | — | — | — |
| E. faecium | 24 h | — | Blue | Pink | Fluo | Blue | — | Blue | Pink | Fluo | Blue |
| | 48 h | Brown | Blue-grey | Pink | Brown + Fluo | Blue-grey | — | Blue | Pink | Fluo | Blue-grey |
| S. pyogenes | 24 h | — | — | — | — | — | — | — | — | — | — |
| | 48 h | Brown | Brown | Brown | Brown | Blue-grey | — | — | — | — | — |
| S. epidermidis | 24 h | — | — | — | — | — | — | — | — | — | — |
| | 48 h | — | — | — | — | Turquoise | — | — | — | — | — |

On media 2, 3 and 4, it is possible, after incubation for 24 hours, to distinguish the *Enterococcus* bacteria (*E. faecium*) which are the only ones to give a coloration other than brown or grey. Media 2, 3 and 4 also make it possible, after culturing for 24 hours, to distinguish the Gram-positive bacteria, which show either an absence of coloration or a coloration other than brown or grey. Media 7, 8 and 9 allow similar distinctions, but after incubation for 48 hours. On medium 5 after incubation for 48 hours, only *S. epidermidis* gives turquoise-coloured colonies, the other bacteria giving brown to blue-grey colonies.

It should be pointed out that when the substrates below are present alone in the reaction medium, the presence of an osidase and the resulting hydrolysis of the 5-bromo-4-chloro-3-indolyl-β-D-glucoside (X-Glu) leads to the appearance of a turquoise-blue colour, the hydrolysis of 6-chloro-3-indolyl-β-D-glucoside (Z-Glu) leads to the appearance of a purple-pink colour. The hydrolysis of 4-methylumbelliferyl-β-D-glucoside (MUGI) leads to the appearance of a blue fluorescence under a UV lamp (wavelength=365 nm) and, in the presence of an esterase, the resulting hydrolysis of 5-bromo-4-chloro-3-indolyl-acetate (X-Ac) leads to the appearance of a turquoise-blue colour.

Example 5

The culture medium contains, besides water:

| | |
|---|---|
| Yeast extract* | 6 g/l |
| Gelatin peptone** | 5 g/l |
| NaCl | 8 g/l |
| Na$_2$CO$_3$ | 0.1 g/l |

*Sold by Bio Mérieux
**Bio-gelytone sold by Bio Mérieux

L-Leu-BIA or L-Ala-BIA is added, alone or combined together, or in combination with 5-bromo-4-chloro-3-indolyl-acetate (X-Ac) to this medium.

The concentrations of these various substrates are as follows:

L-Leu-BIA: 300 mg/l
L-Ala-BIA: 300 mg/l
X-Ac: 200 mg/l

The media obtained were distributed into microtitration plates and inoculated with microorganism suspensions, as above. The plates were incubated for 48 hours at 37° C. The colours of the wells obtained after incubation for 24 and 48 hours are presented in Table V:

TABLE V

| Strains | Medium No. | L-Leu—BIA 1 | L-Ala—BIA 2 | L-Ala—BIA + L-Leu—BIA 3 | L-Ala—BIA + X-Ac 4 |
|---|---|---|---|---|---|
| E. coli | 24 h | — | Brown | Brown | Grey |
| | 48 h | Brown | Brown | Brown | Grey |
| K. pneumoniae | 24 h | Brown | Brown | Brown | Grey |
| | 48 h | Brown | Brown | Brown | Grey |
| C. freundii | 24 h | Brown | Brown | Brown | Grey |
| | 48 h | Brown | Brown | Brown | Grey |
| P. aeruginosa | 24 h | Brown | Brown | Brown | Grey |
| | 48 h | Brown | Brown | Brown | Grey |
| S. agalactiae | 24 h | — | — | Brown | Blue-grey |
| | 48 h | — | Brown | Brown | Blue-grey |
| E. faecium | 24 h | — | — | Brown | Blue-grey |
| | 48 h | — | — | Brown | Blue-grey |
| S. pyogenes | 24 h | — | — | Brown | Blue-grey |
| | 48 h | Brown | Brown | Brown | Grey-brown |
| S. epidermidis | 24 h | — | — | — | Turquoise |
| | 48 h | — | — | — | Turquoise |

It is seen that with the media 3 and 4, it is possible to distinguish *S. epidermidis* from the other bacteria. With medium 1, it is possible to distinguish the Gram-negative bacteria from the Gram-positive cells (except for *S.* pyogenes) after incubation for 48 hours. Medium 2 allows differentiation of the Gram-positive and Gram-negative bacteria after incubation for 24 hours.

Example 6

The culture medium contains, besides water:

| | |
|---|---|
| Beef extract* | 3 g/l |
| Gelatin peptone** | 5 g/l |
| NaCl | 8 g/l |
| Agar | 15 g/l |

*Sold by Bio Mérieux
**Bio-gelytone sold by Bio Mérieux

L-Ala-BIA or L-Ala-AMC is added to this medium, to concentrations of 300 mg/l and 200 mg/l respectively. The various media obtained, distributed into Petri dishes, are inoculated with microorganisms. The dishes are incubated at 370° C. for 48 hours. The colonies formed were examined visually in ambient light and under a UV lamp as above, after incubation for 24 and 48 hours. The colour or the presence of fluorescence were noted. The results are presented in Table VI below.

TABLE VI

| Strain | | L-Leu—AMC | L-Leu—BIA |
|---|---|---|---|
| E. coli | 24 h | Fluo[1] | Brown |
| | 48 h | Fluo | Brown |
| K. pneumoniae | 24 h | Fluo | Brown |
| | 48 h | Fluo | Brown |
| C. freundii | 24 h | Fluo | Brown |
| | 48 h | Fluo | Brown |
| P. aeruginosa | 24 h | Fluo | — |
| | 48 h | Fluo | Brown |
| S. agalactiae | 24 h | —[2] | — |
| | 48 h | Fluo | — |
| E. faecium | 24 h | — | — |
| | 48 h | Fluo | — |
| S. pyogenes | 24 h | — | — |
| | 48 h | Fluo | Brown |
| S. epidermidis | 24 h | — | — |
| | 48 h | — | — |
| C. albicans | 24 h | — | — |
| | 48 h | Fluo | Brown |

TABLE VI-continued

| Strain | L-Leu—AMC | L-Leu—BIA |
|---|---|---|

[1]Fluo = fluorescence
[2]— = absence of fluorescence and/or absence of coloration With the medium used in this example, it is thus possible to demonstrate the L-alanine-aminopeptidase activity with L-Ala-AMC as well as with L-Ala-BIA.

I claim:

1. A microorganism culture medium containing, besides the ingredients necessary for culturing microorganisms, at least one compound of formula:

X—NH—R in which X represents a 5-bromoindol-3-yl group and R represents the acyl residue of an amino acid chosen from leucine and alanine.

2. The culture medium according to claim 1, containing from 25 to 2000 mg/l of the said compound.

3. The culture medium according to claim 1, wherein the culture medium is a gelled medium.

4. A method for demonstrating a peptidase activity in a microorganism culture, wherein a tracer, which makes it possible to demonstrate said peptidase activity by formation of a colored product, is added to a culture medium of microorganisms, said tracer comprising at least one compound of formula:

X—NH—R in which X represents a 5-bromoindol-3-yl group and R represents an acyl residue of an amino acid chosen from leucine and alanine.

5. The method according to claim 4, wherein R represents an acyl residue of L-Leu, L-Ala or D-Ala.

6. The method according to claim 4, wherein said culture medium is a gelled medium.

7. The method according to claim 4, wherein said culture medium is a liquid medium.

8. The method according to claim 4, wherein at least one other tracer is added to the culture medium, wherein said at least one other tracer makes it possible to demonstrate, by formation of a colored or fluorescent product, an enzymatic activity different from said peptidase activity.

* * * * *